United States Patent [19]

Lewin et al.

[11] Patent Number: 5,582,987
[45] Date of Patent: Dec. 10, 1996

[54] METHODS FOR TESTING BOVINE FOR RESISTANCE OR SUSCEPTIBILITY TO PERSISTENT LYMPHOCYTOSIS BY DETECTING POLYMORPHISM IN BOLA-DR3 EXON 2

[75] Inventors: Harris A. Lewin, Champaign; Michiel J. T. van Eijk, Urbana, both of Ill.

[73] Assignee: The Board of Trustees of The University of Illinois, Urbana, Ill.

[21] Appl. No.: 300,853

[22] Filed: Sep. 6, 1994

Related U.S. Application Data

[63] Continuation of Ser. No. 852,853, Mar. 17, 1992, abandoned.
[51] Int. Cl.$^6$ .............. C12Q 1/68; C12P 19/34; C07H 21/04
[52] U.S. Cl. .............. 435/6; 435/912; 536/24.33; 536/24.31; 935/77; 935/78
[58] Field of Search .............. 435/6, 91.2; 536/24.33, 536/24.31; 935/77, 78

[56] References Cited

U.S. PATENT DOCUMENTS

| | | | |
|---|---|---|---|
| 4,683,195 | 7/1987 | Mullis et al. | 435/91.2 |
| 5,041,371 | 8/1991 | Cowan et al. | 435/6 |

OTHER PUBLICATIONS

Signaclarclottir et al. Amin. Genet. 22:199–209 (1991).
Lewin J. Dairy Sci 72:1334–1348 (1989).
Bernoco et al. Amim. Genet. 22:477–496 (1991).
Anderson et al. Amim. Genet. 17:295–304 (1986).
Lewin et al Immungenet. 27:338–344 (1988).
Groenen et al. Immunogenet. 31:37–44 (1990).
Van der Poel et al. Immunogenet. 31:29–36 (1990).
Joosten et al. Immunogenet 31:123–126 (1990).
Muggli–Cockett et al. Amim. Genet. 19:213–225 (1988).
Anderson. et al. Amim. Genet 17:95–112 (1986).
Stone et al. Amim. Genet. 21:353–360 (1990).
Sigurdurdottir. et al. Amim Genet 19:133–150 (1988).

Primary Examiner—Stephanie W. Zitomer
Assistant Examiner—Lisa Arthur

[57] ABSTRACT

The present disclosure provides a method for evaluating resistance of an animal of the genus Bos to persistent lymphocytosis. The method includes the steps of (a) obtaining a sample of DNA from the animal that includes a DRB3 gene exon 2; (b) identifying nucleotides of the DRB3 gene exon 2; and (c) determining whether the nucleotides contain codons that encode a glutamic acid at position 70 and an arginine at position 71, a valine at position 75, an aspartic acid at position 76, a threonine at position 77, and a tyrosine at position 78 of the DRB3 gene product, the presence of which codons indicates susceptibility to persistent lymphocytosis. Kits containing primers that hybridize to nucleotide positions 70 and 71 or 75–78 of the DRB3 gene exon 2 are also provided.

12 Claims, 9 Drawing Sheets

FIG. 6b

```
3'-GACCTTCCTCTCCGCCCG-5'         ER-primer              Motif (70-71)
5'-CTGGAGGAGAGGCGGGC-3'          DRB3.2*11, *23, *28    ER
------A------                    DRB3.2*24              EK
------CG-G------                 DRB3.2*8               RG
------CG-GA------                DRB3.2*16              RE
------CG------                   DRB3.2*22              GR 3'-CACCTGTGCATGACGTCTG-5'        VDTY-primer            Motif (75-78)
5'-GTGGACACGTACTGCAGAC-3'        DRB3.2*8, *16          VDTY
------G-GTG------                DRB3.2*11, *23, *24, *28   VDRY
------GTG------                  DRB3.2*22, *26         VDTY
```

| ID# | 14 | 15 | 16 | 17 | 18 | 19 | 20 | 21 | 22 | 23 | 24 | 25 | 26 | M |
|---|---|---|---|---|---|---|---|---|---|---|---|---|---|---|
| PL | + | + | + | + | + | + | + | + | + | + | + | + | + | |
| DRB3 | 22/22 | 22/8 | 27/16 | 8/24 | 16/24 | 22/24 | 3/3 | 16/24 | 16/27 | 22/16 | 22/8 | 8/8 | 16/24 | |
| Motif ER | – | – | – | – | – | – | – | – | – | – | – | – | – | |
| Motif VDTY | – | + | + | + | + | – | +/+ | + | + | + | + | +/+ | + | |
| Motif VDTV | +/+ | + | – | – | – | + | – | – | – | + | + | – | – | |
| Motif VDRV | – | – | + | + | + | + | – | + | + | – | – | – | + | |

FIG. 7a

| ID# | M | 1 | 2 | 3 | 4 | 5 | 6 | 7 | 8 | 9 | 10 | 11 | 12 | 13 |
|---|---|---|---|---|---|---|---|---|---|---|---|---|---|---|
| PL | | – | – | – | – | – | – | – | – | – | – | – | – | – |
| DRB3 | | 28/11 | 22/28 | 24/23 | 22/11 | 16/28 | 8/11 | 12/11 | 3/11 | 27/28 | 27/16 | 22/16 | 8/11 | 22/24 |
| Motif ER | | +/+ | + | + | + | + | + | + | + | – | – | – | – | – |
| Motif VDTY | | – | – | – | – | + | + | + | + | + | + | + | + | – |
| Motif VDTV | | – | + | – | + | – | – | – | – | – | – | + | – | + |
| Motif VDRV | | +/+ | + | +/+ | + | + | + | + | + | + | + | – | + | + |

FIG. 7b

METHODS FOR TESTING BOVINE FOR RESISTANCE OR SUSCEPTIBILITY TO PERSISTENT LYMPHOCYTOSIS BY DETECTING POLYMORPHISM IN BOLA-DR3 EXON 2

This invention was made with government support under competitive research grants 89-37266-4568 and 91-37205-6355, awarded by the U.S. Department of Agriculture. The United States government has certain rights in the invention.

This application is a continuation of application Ser. No. 07/852,853, filed on Mar. 17, 1992, now abandoned entitled BOVINE AND GENETIC MARKERS AND METHODS OF TESTING OF AND USING SAME.

This application is related to Disclosure Document No. 303,437 filed Feb. 24, 1992 entitled, "Bovine Genetic Markers and Genotyping of Oocytes", the entirety of which is hereby incorporated by reference.

BACKGROUND OF THE INVENTION

The bovine lymphocyte antigen ("BoLA") system is the major histocompatibility complex ("MHC") of cattle (Amorena et al., *Science* 201:159–160 (1978), Spooner et al., *J. Immunogenetics* 5:335–346 (1978)) and, as in most mammals, contains several highly polymorphic class I and II genes (Bernoco et al., *Animal Genetics* 22:477–496 (1992)). These genes encode cell-surface molecules whose function is the presentation of antigenic peptides to T-cells (Allen et al., *Immunological Reviews* 98:171–187 (1987)); thereby, playing an essential role in the immune response to foreign agents. In humans, numerous associations between MHC genes and predisposition to disease have been reported (Tiwari et al., *HLA and Disease Associations* 472 (1985)). Although most of these associations in humans involve diseases of unknown etiology, research in cattle is conducted primarily to investigate whether the BoLA system is associated with immune responsiveness to microbial antigens and susceptibility to infectious diseases (Lewin, *J. Dairy Science,* 72:1334–1348 (1989); Lewin et al., *Gene-mapping: Techniques and Applications* 283–303 (1991)).

The BoLA class II genes appear to be organized in a similar fashion to those of humans (Bensaid et al., *Gene-mapping: Techniques and Applications* 127–158 (1991)). There is evidence for the existence of two DQA and DQB genes, one DRA and three DRB genes (one of which is a pseudogene), and one gene for DNA, DOB, and the novel genes DIB, DYA, and DYB (Andersson et al., *Animal Genetics* 17:95–112, 17:295–304 (1986); Andersson et al., *Immunogenetics* 27:273–280 (1988); Andersson and Rask *Immunogenetics* 27:110–120 (1988); Muggli-Cockett et al., *Animal Genetics* 19:213–225 (1988), 20:361–370 (1989); Stone et al., *Animal Genetics* 21:353–360 (1990)). At least one BoLA-DQB and one BoLA-DRB gene is expressed based on cDNA cloning experiments (Xu et al., *Animal Genetics* 22:381–398 (1991), Burke et al., *Animal Genetics* 22:343–352 (1991)) Recent studies indicate that DRB3 is the most actively transcribed gene for the BoLA-DRB subregion, whereas the DRB2 gene is not expressed or is transcribed at a much lower level (Burke et al., 1991.

Several methods have been used to characterize the polymorphism of BoLA class II gene products and genes. Serology and one-dimensional isoelectric focusing ("1-D IEF") have been used for studying protein polymorphism, and restriction fragment length polymorphism ("RFLP") and DNA sequencing for elucidating the genetic organization and polymorphism of BoLA genes (Bernoco et al., 1992; Sigurdardóttir et al., *Animal Genetics* 22: 199–209 (1991)) Characterization of BoLA class II products by 1-D IEF has resulted in the definition of 11 allelic patterns of a DRB-like locus (Joosten et al., *Immunogenetics* 29:213–216 (1989)), whereas the serological approach distinguished four B cell specific alloantigens (Davies et al., *Animal Genetics* 22:417–434 (1991)). Analysis of the BoLA class II genes by RFLP has revealed 30 DQ and 31 DR RFLP-defined haplotypes (Sigurdardóttir et al., *Animal Genetics* 19:133–150 (1988); Joosten et al., *Immunogenetics* 31:123–126 (1990); Bernoco et al., (1992)).

The availability of sequence data for human leukocyte antigen ("HLA") genes (Marsh et al., *Immunogenetics* 33:321–334 (1991), and the advent of the polymerase chain reaction ("PCR") technology (Saiki et al., *Science* 239:487–491 (1988)) have been instrumental in the development of sequence-based HLA typing methods. These methods employ single strand oligonucleotides (Erlich et al., *European J. Immunogenetics* 18:33–55 (1991)) or restriction endonucleases (PCR-RFLP—Dekker et al., *Immunogenetics* 32:56–59 (1990); Maeda et al., *Tissue Antigens* 34:298–298 (1989), *Human Immunology* 27:111–121 (1990); Uryu et al., *Tissue Antigens* 35:20–31 (1990)) for the identification of polymorphism in amplification products of HLA class II genes. The latter method was shown to be very powerful for the detection of polymorphism in the exon encoding the B1-domain of DPB1, DQA1, DQB1, DQB2, DRB1, DRB3, and DRB4. With the assistance of the recent publication of nucleotide sequences of 14 BoLA-DRB3 alleles (Sigurdardóttir et al., (1991)), it was determined that PCR-RFLP could be useful for BoLA-DRB3 typing.

Development of a primary physical map of the bovine genome has been aided by the application of comparative gene mapping strategies. Phylogenetically conserved chromosomal segments, some consisting of up to 17 genes, have been identified primarily using a panel of bovine-hamster somatic hybrids and by in situ hybridization (Womack, *Gene Mapping: Techniques and Applications* 3–20 (1991)). Although approximately 250 genes have now been assigned to chromosomes or syntenic groups (Womack et al., in press in *Cytogenetic Cell Genetics*), less than 50 genes are included in the bovine linkage map (Fries et al., *Animal Genetics* 20:3–29 (1989)). As a consequence of the sparseness of the bovine linkage map, there is very little comparative linkage data for cattle and humans.

The human genes for prolactin ("PRL") and the HLA system are located on the short arm of chromosome 6 (Lamm et al., *Human Heredity* 24:273–284 (1974); Owerbach et al., *Science* 212:815–816 (1981)). Detailed physical and genetic maps exist for the HLA region (Spence et al., *Cytogenetic Cell Genetics* 51:149–165 (1989)), but the order of PRL relative to other genes in the 6p23-21.1 interval has not been determined. The lack of genetic mapping data for PRL can be attributed to the absence of known polymorphic markers at this locus.

In cattle, PRL and the bovine major histocompatibility complex (BoLA) have been mapped to chromosome 23 by in situ hybridization (Fries et al., *Animal Genetics* 17:287–294 (1986); Hailerman et al., *Animal Genetics* 19:123–131 (1988)), forming a conserved synteny with humans, but not with rats (Lalley et al., *Cytogenetic Cell Genetics* 51:503–532 (1989)). Present knowledge of the genes in the BoLA linkage group includes the BoLA class I and II genes, C4, Bf, HSP70, the TCP1 locus and the M blood group (Fries et al., 1989). The BoLA class I and class II genes are highly polymorphic (Bernoco et al., 1992), and like their human and murine homologs are known to govern interactions between cells of the immune system (Glass et al., *Animal Genetics* 21:15–28 (1990)).

Polymorphism in the coding regions of bovine PRL has been previously identified by cDNA sequencing (Sasavage et al., *J. Biol. Chemistry* 257:678–681 (1982)). Recently, RFLP analysis in a large paternal half-sib family of Holstein-Friesian cattle revealed a PRL-linked quantitative trait locus ("QTL") affecting milk production (Cowan et al., *Theoretical and Applied Genetics* 79:577–582 (1990)). The independent observations of BoLA-linked disease resistance and the PRL-associated QTL for milk yield provided compelling reasons to determine the genetic distance between these loci. Thus, determination of genetic linkage acquires an increased importance.

Sperm typing is a powerful new method for constructing genetic linkage maps (Li et al., *Nature* 335:414–417 (1988); Arnheim et al., *Genomics* 8:415–419 (1990)). It is the most efficient method for accurate estimation of genetic distances between very closely linked loci due to the large number of meiotic products available in a typical sperm sample. The sperm typing technique was used to accurately measure recombination between linked loci (Cui et al., *Proc. Natl. Acad. Sci.* 86:9389–9393 (1989)) and to order DNA markers in a three point cross (Goradia et al., *Genomics* 10:748–755 (1991)). Sperm typing has the additional advantage of being able to employ loci with limited polymorphism (Hubert et al., submitted to *Genomics*) since doubly and triply heterozygous donors for most loci can be found in a sperm collection of about 100 samples (Boehnke et al., *Am. J. Human Genetics* 45:21–32 (1989)).

OBJECTS OF THE INVENTION

It is therefore an object of the present invention disclosed and described herein to provide for a method and means for elucidating alleles of a given locus by detecting DNA polymorphism.

It is an another object to determine the extent of such polymorphism without the need of radioisotopes.

It is a further object to elucidate linkage between polymorphic loci and other loci which produce a phenotype, trait, potential, or predisposition of interest.

It is still a further object to provide for a diagnostic assay which employs amino acid motifs of interest to differentiate or discriminate among alleles.

Other objects, features, and advantages of the present invention will be apparent from the accompanying description, sequence data, and tables and figures.

SUMMARY OF THE INVENTION

One major aspect of this invention involves a method and means for elucidating the number and nature of the alleles of the bovine lymphocyte antigen system, herein the method specifically involves cattle. A polymerase chain reaction-based method is described for typing of alleles of the bovine lymphocyte antigen DRB3 gene ("BoLA-DRB3"). A total of 35 DRB3 alleles have been distinguished by digestion of PCR amplification products of BoLA-DRB3 exon 2 with RsaI, BstYI and HaeIII; however, 3 of these alleles still must be confirmed by segregation in families. This method is herein called polymerase chain reaction-restriction fragment length polymorphism typing ("PCR-RFLP typing").

All restriction fragment patterns, with the exception of one HaeIII pattern, were consistent with restriction sites that were found among 14 previously sequenced DRB3 alleles. The PCR-RFLP typing method was evaluated on 168 genomic DNA samples collected from animals of 10 cattle breeds, 48 of which were typed in the Fourth International BoLA Workshop for BoLA-DRB and BoLA-DQB by conventional RFLP analysis using heterologous and homologous DNA probes. Thirty-one DRB/DQB haplotypes containing 23 DRB3 alleles were identified among the 48 workshop animals analyzed. Using PCR-RFLP, 11 DRB3 alleles were identified in 18 workshop animals for which DRB RFLPs were not informative. PCR-RFLP typing of additional animals revealed seven new DRB3 alleles, of which three contained a putative 3 base pair deletion in the identical position as found for the sequenced allele DRB*2A (See Table 1). PCR-RFLP was shown to be a rapid and sensitive method for the detection of polymorphism in a functionally relevant domain of the BoLA-DRB3 gene and will be useful for studying the evolution of DRB polymorphism in cattle and other Bovidae.

Another major aspect of this invention involves linkage between the MHC and PRL. The MHC and PRL genes are syntenic in man and cattle but heretofore the genetic distance between these loci has not been determined for either species. Here, a sperm typing technique was used to measure the recombination frequency between the BoLA-DRB3 and PRL loci. A total of 300 sperm were typed from one doubly heterozygous bull for segregation of DRB3 and PRL alleles. Sperm typing was performed using the PCR-RFLP typing method. Digestion with the RsaI allowed the unambiguous discrimination of alleles for both loci. The maximum likelihood estimation of the recombination fraction $\theta=0.04$, with a 95% confidence interval of 0.01 to 0.07. Close linkage between PRL and DRB3 has important implications for marker-assisted selection in animal breeding since PRL has been shown to be closely linked to a locus that affects milk yield, and BoLA loci influence susceptibility to a number of infectious diseases. The relationship between BoLA polymorphism and resistance to infectious diseases has been described and selection based on BoLA genotype has been suggested as a means of achieving resistance to specific diseases (Lewin et al., 1991). The close linkage between BoLA-DRB3 and PRL may be of practical significance for additional reasons as well. Recently, Cowan et al. (1990) found that the progeny of a bull that inherited one RFLP-defined PRL allele had greater genetic potential for milk production than offspring that inherited the alternative paternal allele, suggesting that PRL or a closely linked gene affects this economically important trait. If this observation is due to linkage, it is reasonable to predict that the closely linked BoLA system will be a better marker than PRL for this QTL (milk production) because BoLA is highly polymorphic, thus enabling the dissection of many more possible haplotypes.

Typing by PCR-RFLP is also useful for creating and/or standardizing other diagnostic assays. Because polymorphism in the BoLA-DRB3 gene correlates to resistance or susceptibility of various bovine diseases affecting cattle, such as persistent lymphocytosis ("PL"), sequence data of the BoLAoDRB3 is useful as a predictor of disease resistance and susceptibility. Based on the results of PCR-RFLP typing of cattle for PL caused by bovine leukemia virus ("BLV") infection, the complete nucleotide sequence of DRB3 alleles from resistant and susceptible animals were determined. Among resistant haplotypes the amino acids glutamic acid (E, in single letter code) and arginine (R) were found exclusively at positions 70 and 71, respectively, of the DRB3 β-chain peptide. Based on the predicted structure of class II molecules, positions 70 and 71 are part of the antigen recognition site contained within the alpha helix and face into the peptide binding groove. Through the use of the PCR-RFLP data, a new diagnostic assay was developed.

With this assay, termed motif discrimination by product length ("MDPL"), no animals with PL (now more than 50 tested) have ever been identified that have E and R at positions 70 and 71. Thus, animals having the E and R motif in at least one allelic DRB3 product is absolutely correlated with resistance to PL. The use of MDPL requires only one motif, E and R, at positions 70 and 71 to predict resistance to PL; whereas with PCR-RFLP, resistance is associated with multiple types, each of which encode E and R at positions 70 and 71. Thus, MDPL simplifies the identification of PL resistance genes.

Susceptibility to PL also has a genetic basis that maps to BoLA-DRB3. Among the DRB3 alleles from susceptibility-associated BoLA haplotypes, the motif valine, aspartic acid, threonine, and tyrosine (V, D, T and Y) at positions 75–78 (part of the DRB3 molecule that is recognized by T cells) was most commonly found in animals with PL. Typing by MDPL can therefore also be used to directly test for susceptibility to PL by detecting V, D, T and Y at positions 75 to 78 and related motifs in the DRB3 gene.

BRIEF DESCRIPTION OF THE TABLES AND FIGURES

Table 1 defines BoLA-DRB3 alleles by PCR-RFLP and shows correspondence these PCR-RFLP alleles to sequenced DRB3 alleles and BoLA-DRB3 and BoLA-DQB RFLP patterns.

Table 2 contains information on BoLA-DQ/DR haplotypes of animals utilized in the Fourth International BoLA workshop. DRB RFLP patterns for these animals could not be defined but PCR-RFLP typing was informative.

Table 3 presents the distribution of observed DRB3 and PRL alleles in 300 typed sperm from one bull.

Table 4 presents the maximum likelihood estimates of the parameters 8 (recombination factor), amplification efficiency, contamination, and sperm sorting for single sperm typing data. The maximum log likelihood estimate was 545.446.

FIGS. 1 $a$, $b$, and $c$ respectively depict the restriction enzyme patterns of the second round PCR product of BoLA-DRB3 exon 2 upon digestion with RsaI, BstYI, and HaeIII. The vertical lines ("|") which intersect the horizontal line representing the sequence indicate the boundary between exon 2 and the flanking introns. Sizes of restriction fragments are indicated between the restriction sites, which are marked by vertical lines ("|") which meet, but do not cross, the horizontal line representing the sequence. Arrows "↓" indicate the presence of a deletion, with putative positions in patterns p, q, and r of FIG. 1$a$; pattern e was confirmed by DNA sequencing. Pattern c in FIGS. 1$b$ and 1$c$ also support the presence of a deletion.

FIG. 2 shows allelic patterns of BoLA-DRB3 exon 2 obtained by digestion of PCR products with RsaI. Lane 1 is a size marker employing a MspI digestion of pBR322. Allelic patterns are indicted at the bottom of lanes 2–9. This gel did not clearly resolve fragments which were smaller than 39 base pairs.

FIG. 3 shows allelic patterns of BoLA-DRB3 exon 2 obtained by digestion of PCR products with RsaI, BstYI, and HaeIII. Lane 1 is a size marker employing a MspI digestion of pBR322. Allelic patterns for RsaI (lanes 2–4), BstYI (lanes 5–7), and HaeIII (lanes 8–10) are indicted at the bottom of the lanes. This gel did not clearly resolve fragments which were smaller than 39 base pairs. Faint 284 and 281 base pair bands were present in lanes 5 and 6 and are respectively heteroduplexes and residual undigested PCR product.

FIGS. 4$a$ outlines the strategy of discriminating BoLA-DRB3 exon 2 (DRB*2A=DRB3.2*7, DRB3*7E=DRB3.2*12; see Table 1) alleles with RsaI. FIG. 4$b$ outlines the strategy of discriminating PRL (PRL*B, PRL*b) alleles with RsaI. The vertical lines ("|") which intersect the horizontal line representing the sequence indicate the boundary between exons and the flanking introns. Triangles "▼" indicate the presence of RsaI restriction sites. Primers are indicated by horizontal arrows ("→" or "←"). The DRB3.2*12 product is 3 base pairs shorter than DRB3.2*7 due to a deletion, which is reflected in the 51 base pair RsaI fragment. These DRB3 patterns correspond to e and h of FIG. 1$a$.

FIG. 5 is an ethidium bromide stained gel of a representative results from the 300 analyzed bull sperm. Lane 1 is a size marker employing a MspI digestion of pBR322. Alleles at each locus are shown separately in lanes 2–5. Linkage phase is shown in lanes 6 and 7. Recombinant genotypes are shown in lanes 8 and 9.

FIG. 6$a$ depicts the general scheme for performing the motif discrimination by product length assay and the amplification products obtained thereby. FIG. 6$b$ depicts the ER (SEQ ID NOS. 8 and 11) and VDTY (SEQ ID Nos. 10 and 12) primers and identifies the alleles detected and differentiated with this assay.

FIG. 7$a$ depicts the results of the motif discrimination by product length assay of 13 cows with persistent lymphocytosis ("PL"). FIG. 7$b$ depicts results with this assay on 13 seropositive non-PL cows which were unrelated and age-matched to the cows identified in FIG. 7$a$.

DETAILED DESCRIPTION OF THE INVENTION

I. Polymorphism of BoLA-DRB3

Figure 1A:
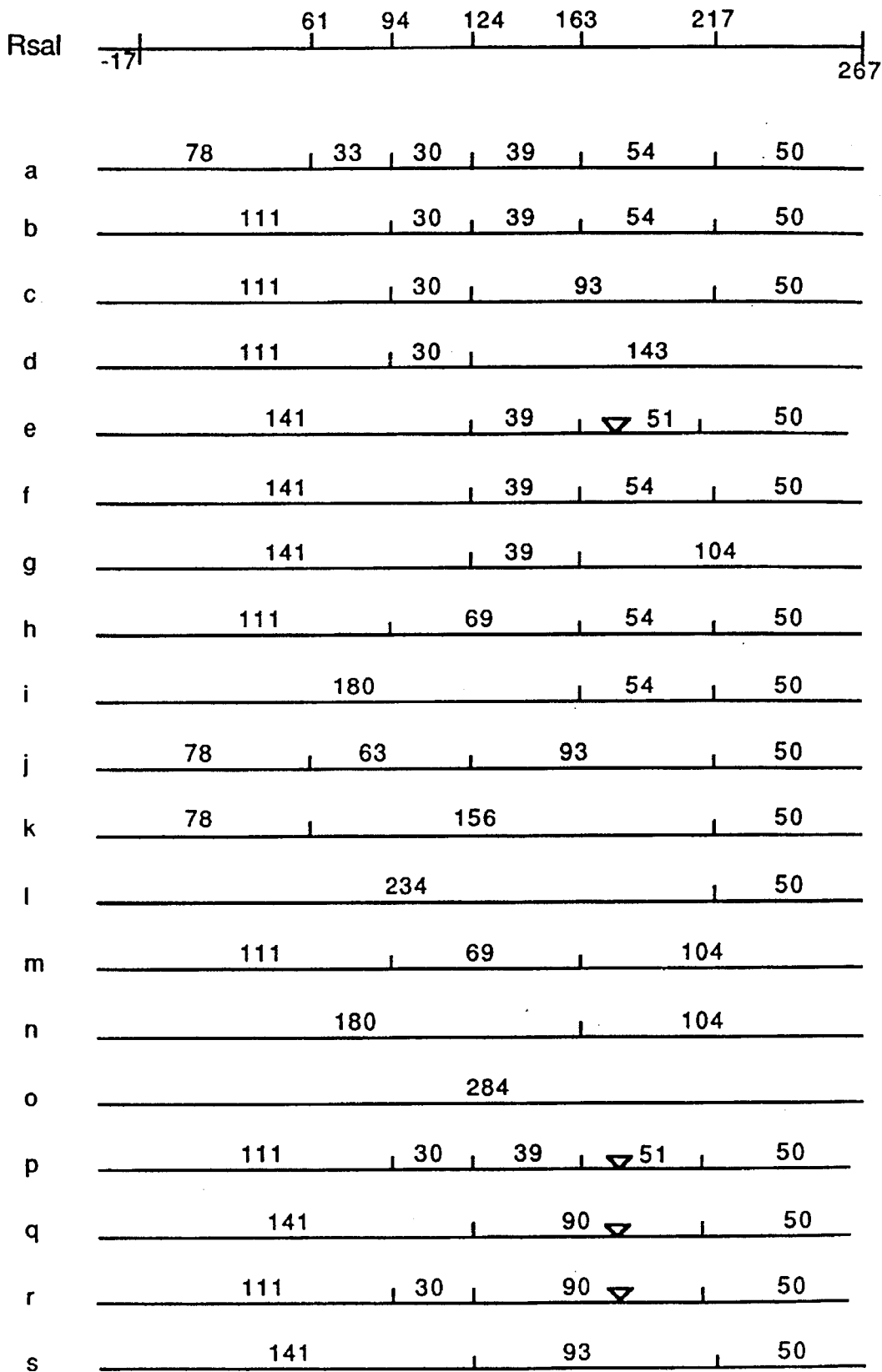

Elucidation of the polymorphism of BoLA-DRB3 by PCR-RFLP was performed as follows:

Animals

One hundred and sixty-eight animals of 10 cattle breeds (Angus, Ayrshire, Brown-Swiss, Gelbvieh, Guernsey, Jersey, Holstein-Friesian, Polled Hereford, Simmental and South Devon) were used in this study. Forty-eight of these animals were typed for BoLA-A antigens and BoLA-DQB and -DRB RFLP patterns as part of the Fourth International BoLA Workshop (Bernoco et al., 1992).

Amplification of BoLA-DRB3 exon 2 by PCR

Genomic DNA was prepared from whole blood or semen as previously described (Miller et al., *Nucleic Acids Research* 16:1215 (1988), Andersson et al., *Animal Genetics* 17:295–304 (1986)) and diluted in distilled water to 10 ng/μl. Oligonucleotide primers used for amplification of the second exon of BoLA-DRB3 were based on previously published sequences of BoLA-DRB3 alleles (Groenen et al., *Immunogenetics* 31:37–44 (1990); Sigurdardóttir et al., (1991)). Amplification of DRB3 alleles was performed in two stages. For the first round of amplification the primers were: HL030: 5' ATCCTCTCTCTGCAGCACATTTCC 3' (SEQ ID NO:1), and HL031: 5' TTTAAATTCGCGCTCAC-CTCGCCGCT 3' (SEQ ID NO:2). The primers HL030 and HL031 contain seven and eight nucleotides of the 5' and 3' ends of exon 2 respectively, plus intron sequences. Hemi-nesting (Li et al., *Proc. Nat. Acad. Sci.* 87:4580–4584 (1990)) was used to increase yield and specificity of the PCR product in the second round of amplification, employing primers HL030 (as above) and HL032; 5' TCGCCGCTGCACAGT-GAAACTCTC 3' (SEQ ID NO:3). HL032 consists entirely of nucleotides at the 3' end of exon 2 and has an eight base pair overlap with the 3' end of HL031.

Reactions were carried out in a 50 µl final volume containing 48 µl PCR buffer (final concentration 50 mM KCl, 10 mM Tris-HCl, 2.5 mMMgCl$_2$, 0.01% gelatin), 100 µM dNTPs, 0.5 µM of each of the DRB3 primers and 1 unit of Taq polymerase (Perkin Elmer, Cetus, Norwalk, Conn.). The thermal cycling profile for the first round of amplification was: initial denaturation for 4 min at 94° C. followed by 10 cycles of 1 min at 94° C., 2 min at 60° C. and 1 min at 72° C. Final extension was for 5 min at 72° C. Subsequently, 2 µl of first round product were transferred to another 500 µl tube containing 48µl PCR buffer (as above) for a second round of PCR according to the following thermal cycling profile: 25 cycles of 1 min at 94° C. and 30 seconds at 65° C., followed by a final extension for 5 min at 72° C. All PCRs were performed in a 60-well thermal cycler (MJ Research, Inc., Cambridge, Mass.).

Selection of Restriction Enzymes for RFLP Analysis

Analysis of 14 sequenced BoLA-DRB3 alleles (Sigurdardóttir et al., (1991)) for restriction endonuclease cleavage sites resulted in the selection of RsaI, BstYl and HaeIII as tools to study polymorphism in exon 2 of the DRB3 gene. This analysis showed that these three enzymes could distinguish all 14 sequenced alleles (Table 1; FIG. 1). Seven sequenced DRB3 alleles (1A, 2A, 4A, 5, 8A, 9A and 11) could be differentiated by RsaI as a result of having polymorphic restriction sites (FIG. 1). Three sequenced DRB3 alleles (3, 6, and 12) could be identified by digestion with RsaI and BstYl and the remaining four (1B, 7A, 10 and 13A) could be distinguished by a combination of the three enzymes. It should be noted, however, that the invention disclosed herein is not limited to the use of the three identified enzymes—other restriction enzymes may also prove to be effective.

Detection of BoLA-DRB3 Alleles

Ten µl of second round PCR product were digested for 1.25 hours at 37° C. with 5 units of either RsaI, HaeIII (Bethesda Research Laboratories, Gaithersburg, Md.) or at 50° C. with 5 units of BstYI (New England Biolabs Inc., Beverly, Mass.) in a total volume of 15 µl. Digestions with BstYI and HaeIII were performed in 60-well Terasaki trays (Robbins Scientific Corp., Sunnyvale, Calif.). Digestions with BstYI were done in 500 µl PCR tubes, using a thermal cycler. After incubation, BstYl digested product was heated to 85° C. for 4 minutes to denature the enzyme in order to obtain clear resolution of the restriction fragments. Restriction fragments were resolved by 6% polyacrylamide gel electrophoresis ("PAGE"), (Hoefer model SE200, Hoefer Scientific Instruments, San Francisco, Calif.) at 25 mA for 45 minutes. A digest of pBR322 with MspI (New England Biolabs Inc., Beverly, Mass.) was used as a standard for determination of restriction fragment size. Fragments were visualized after staining with ethidium bromide (1 µg/ml) for 5 minutes, and exposure to high speed black and white film (Polaroid 667, Polaroid Corp., Cambridge, Mass.) for 1 to 5 seconds under UV illumination. Detection of alleles is based upon size differentiation of digested PCR products. This method should also be effective at elucidating alleles in other polymorphic loci.

Nomenclature of BoLA-DRB3 Alleles Detected by PCR-RFLP

A nomenclature has not been officially established for alleles of BoLA genes using sequence-based typing methods. Alleles of the BoLA-DRB3 gene as defined by PCR-RFLP will be indicated herein by the format 'locus.exon*allele' (e.g. DRB3.2*1). Thus, identifiers employing both a period and an asterisk will only be used for BoLA-DRB3 alleles defined by PCR-RFLP. This nomenclature was adopted to avoid overlap with the haplotype-based nomenclature for DNA sequences of BoLA-DRB3 exon 2, used by Sigurdardóttir et al., (1991). Other identifying formats used herein correspond to previous usage. See Table 1. This table depicts correspondence between the DRB3 exon 2 alleles defined by PCR-RFLP and other previously known alleles. The column entitled "DRB3 DNA sequence" is for alleles that had been previously sequenced (Sigurdardóttir et al., (1991)). The columns entitled "DRB-RFLP" and "DQB-RFLP" are listed in order that corresponds to observation in DRB/DQB haplotypes.

Usefulness of PCR-RFLP to Characterize BoLA-DRB3

Figure 1B:
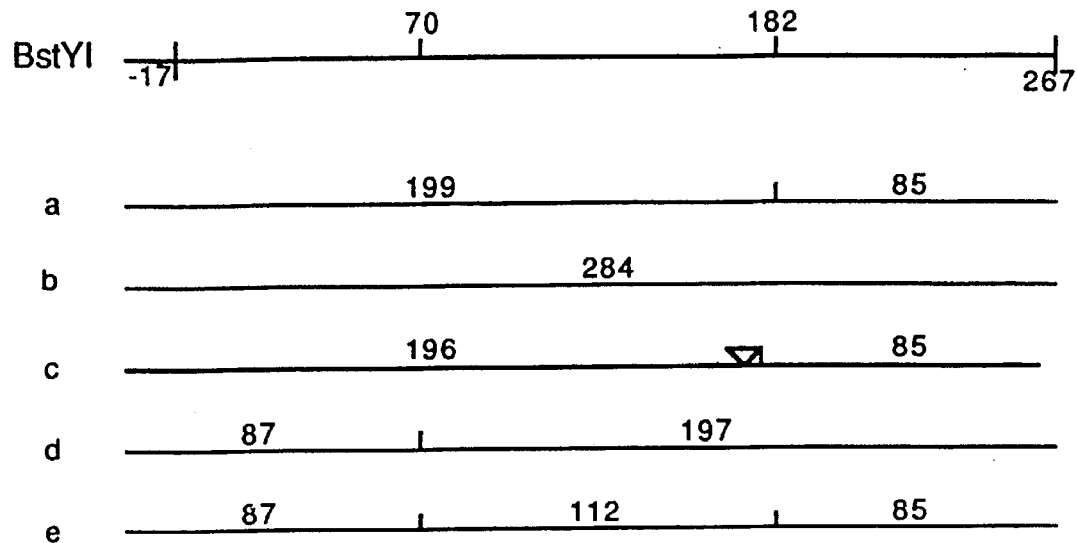
Figure 1C:
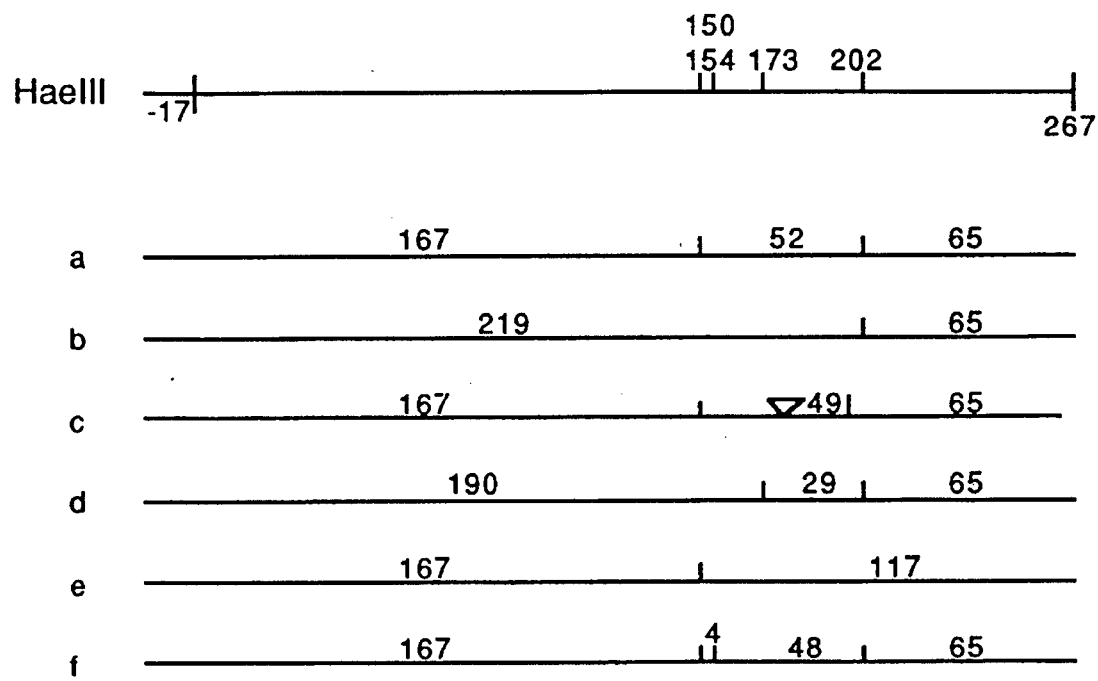
Figure 2:
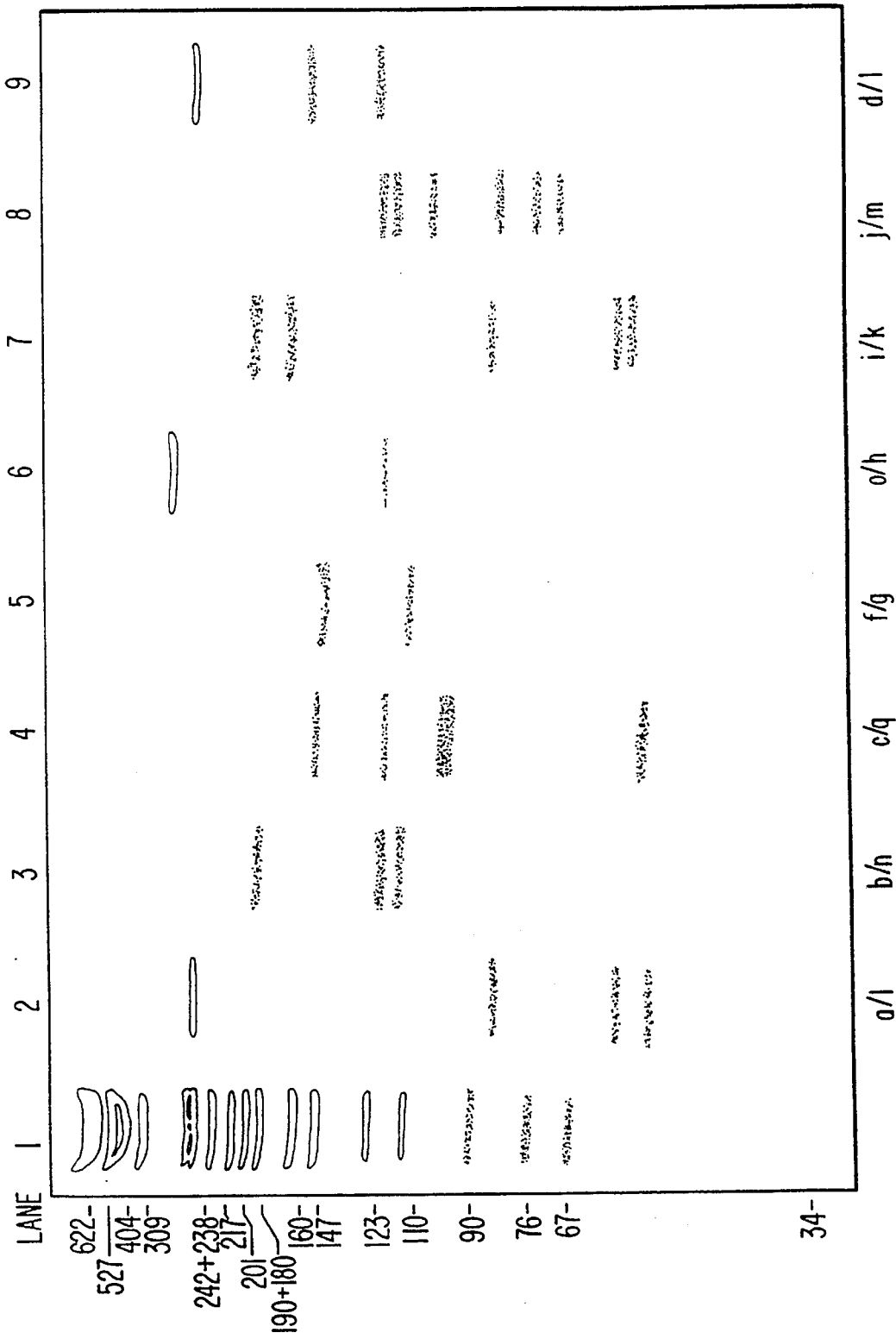
Figure 3:
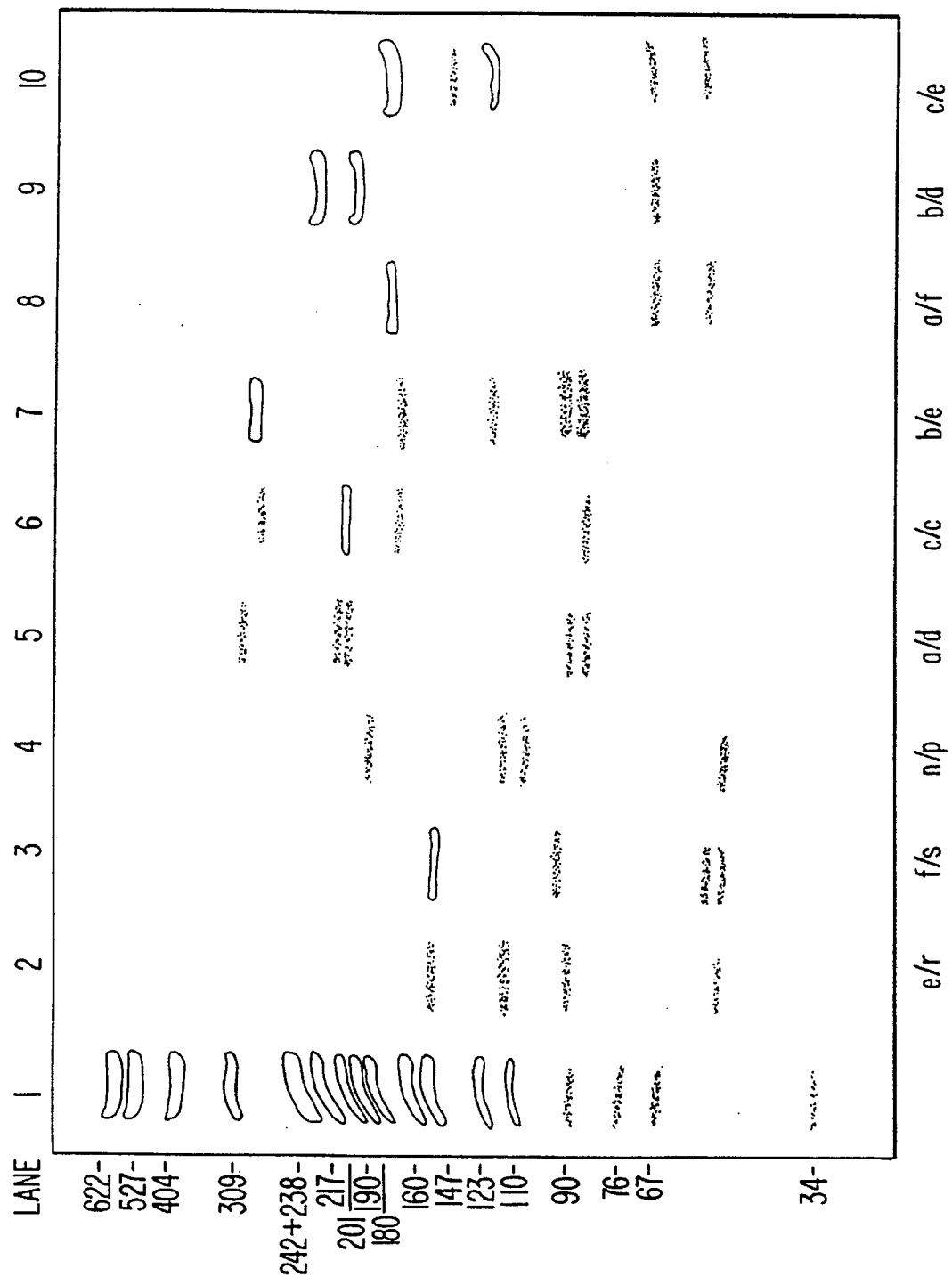

Digestion of amplified BoLA-DRB3 exon 2 products with RsaI resulted in 19 distinct fragment patterns (FIGS. 1a, 2 and 3), 10 of which are associated with known DRB3 sequences. The RsaI restriction sites in the remaining nine patterns (c, d, i, j, k, p, q, r, and s) were inferred from sizes of the restriction fragments. Similarly, five BstYl patterns and six HaeIII patterns were identified (FIG. 1b, 1c and 3). With the exception of HaeIII pattern d, all HaeIII and the five BstYl patterns were found among the 14 sequenced alleles. These patterns, based on differential fragmentation of exon 2, are a result of polymorphism in exon 2 which affects restriction sites in this exon and permits detection and characterization of the alleles. The combination of allelic patterns obtained with the three enzymes led to the identification of 32 DRB3 alleles (Table 1), the majority of which have been subsequently confirmed by segregation in families; 3 other alleles have also been putatively identified and remain to be confirmed by segregation analysis. Other alleles may also exist based on theoretical calculations, see below. Based on DRB RFLP-defined haplotypes within the panel of 48 workshop cells tested, these animals were predicted to contain 12 out of 14 of the sequenced DRB3 alleles. The PCR-RFLP patterns observed for these 12 alleles has been determined to exactly matched the patterns predicted from DNA sequences.

TABLE 1

| PCR-RFLP DRB3 allele | patterns | | | DRB3 DNA sequence | DRB-RFLP | DQB-RFLP |
|---|---|---|---|---|---|---|
| | Rsal | BstYl | Haelli | | | |
| 1 | a | a | a | 5 | 5 | 5 |
| 2 | b | b | a | 13A | 13A | 13A |
| 3 | b | b | b | 10 | 10 | 10 |
| 4 | c | a | a | | — | 3A |
| 5 | c | b | b | | | |
| 6 | d | a | a | | | |
| 7 | e | c | c | 2A | 2A | 2 |
| 8 | f | a | a | 12 | 12B | 12 |
| 9 | f | d | a | 3 | 3C, — | 3B |
| 10 | f | b | a | | 11, 8A | 11B, 14 |
| 11 | g | e | a | 9A | 9A, —, — | 9A, 3A, 3B |
| 12 | h | a | a | | 7E, — | 7E, 13C |
| 13 | h | b | a | 4A | 4A | 4A |
| 14 | h | b | b | | — | 3B |
| 15 | i | b | a | | — | 3B |
| 16 | j | b | d | | 11 | 11C |
| 17 | k | b | b | | 11E | 11E |

TABLE 1-continued

| PCR-RFLP DRB3 allele | patterns Rsal | patterns BstYl | patterns Haelli | DRB3 DNA sequence | DRB-RFLP | DQB-RFLP |
|---|---|---|---|---|---|---|
| 18 | 1 | b | a |  | 5B, — | 5, 6B |
| 19 | 1 | b | f |  |  |  |
| 20 | 1 | b | b |  | — | 1B |
| 21 | 1 | b | e | 8A | 8A | 8 |
| 22 | m | b | a | 11 | 11, — | 9B, 4A |
| 23 | n | b | a |  | 7D, — | 7D, 3B |
| 24 | n | b | b | 1A | 1A | 1A |
| 25 | o | a | a |  | 6 | 6A |
| 26 | o | a | b | 6 | 6 | 6A |
| 27 | o | b | f | 1B | 1B | 1B |
| 28 | o | b | b | 7A | 7A, — | 7A |
| 29 | p | c | c |  |  |  |
| 30 | q | c | c |  |  |  |
| 31 | r | c | c |  |  |  |
| 32 | s | b | b |  |  |  |

Alleles with Deletions

The DRB*2A allele (see Table 1 where this allele is designated DRB3.2*7) has a 3 base pair deletion at nucleotide positions 178–180, which corresponds to codon 65. Digestion of PCR product from DRB*2A with RsaI results in a 51 base pair fragment (pattern e), in lieu of the 54 base pair fragment found in pattern f, which is otherwise identical with respect to the combination of RsaI sites found in pattern e (FIGS. 1 and 3). Three other allelic RsaI patterns, p, q, and r, are consistent with a 3 base pair deletion at the same position. The presence of a deletion is supported by BstYI pattern c and HaeIII pattern c (FIGS. 1b, 1c and 3), both of which have a fragment that is 3 base pair shorter than the corresponding fragment in alleles that do not have a deletion. Based on PCR-RFLP, for DRB3.2*29, the deletion must be between RsaI 163 and BstYI 182 (FIG. 1a pattern p; FIG. 1b pattern c; and FIG. 3, lanes 4 and 6). For DRB3.2*30 and *31 the deletion must be between HaeIII 150 and BstYI 182 (FIG. 1b pattern c; FIG. 1c pattern c; and FIG. 3, lanes 6 and 10). Therefore, although the 32 alleles have thus far been identified as of this date (Table 1), these 32 alleles are actually the result of 28 combinations of polymorphic RsaI, BstY1 and HaeIII sites in DRB3 exon 2. The remaining four alleles (DRB3.2*7, *29, *30, and *31) have restriction sites matching those of other alleles but are distinguished by length variation of fragments due to the presence of a deletion. DRB3.2*29, *30 and *31 have thus far only been identified in South Devon, Angus and Gelbvieh, respectively, whereas DRB3.2*7 has been found in Angus, Gelbvieh and Holstein-Friesian cattle.

PCR-RFLP typing of Fourth BoLA Workshop Animals

Among the 48 animals typed for DRB haplotype by RFLP analysis in the Fourth BoLA Workshop, 16 allelic patterns were defined (Bernoco et al., 1992). Up to 10 new DRB RFLP patterns were inferred in 18 animals but the band composition of these patterns could not be distinguished and thus were not named by the workshop. Using PCR-RFLP, 23 DRB3 alleles were identified in 48 workshop animals. In all 18 workshop animals with an undefined DRB RFLP type, the DRB3 alleles were clearly distinguished by PCR-RFLP (Table 2). Among these 18 animals, 11 DRB3 alleles (DRB3.2*4, *9, *11, *12, *14, *15, *16, *18, *20, *22 and *23) must represent DRB3 alleles for which no DNA sequences have been reported; a conclusion which is based on the observed restriction fragment patterns.

Relationships between BoLA-DRB3 Alleles Detected by PCR-RFLP and BoLAoDRB RFLP Patterns The majority of DRB RFLP-defined haplotypes were associated with a single DRB3 PCR-RFLP allele, but three DRB RFLP-defined haplotypes were split by PCR-RFLP. DRB*8A was found with two PCR-RFLP subtypes, DRB3.2*10 and DRB3.2*21. The DRB*11 RFLP type was associated with three distinct DRB3 PCR-RFLP alleles, DRB3.2*10, DRB3.2*16 and DRB3.2*23. The DRB3 gene in DRB*6 haplotypes was associated with two subtypes, DRB3.2*25 and DRB3.2*26.

Some DRB RFLP types were more informative for distinguishing DRB haplotypes than PCR-RFLP typing (see Table 1). DRB3.2*10 was associated with two RFLP-defined DRB haplotypes, DRB*8A and DRB*11. Five other DRB3 alleles (DPB3.2*9, *12, *18, *22, and *23) were present in two DRB haplotypes. DRB3.2*11 was found in three DRB haplotypes, two of which had RFLP patterns that were not defined by the workshop. In addition, seven distinct DRB3 alleles were found in animals that were not RFLP typed (Table 1). These are: DRB3.2*5 and DRB3.2*30 (Angus), DRB3.2*6 (Simmental), DRB3.2*19 (Holstein-Friesian), DRB3.2*29 and DRB3.2*32 (South Devon), and DRB3.2*31 (Gelbvieh).

TABLE 2

| ANIMAL NUMBER | TYPING INFORMATION | | | | | |
|---|---|---|---|---|---|---|
| FOURTH BOLA WORKSHOP | DQ-RFLP | | DR-RFLP | | DRB3 PCR-RFLP | |
| | 1ST | 2ND | 1ST | 2ND | 1ST | 2ND |
| 2 | 1A | 3A | 1A | — | 24 | 11 |
| 3 | 12 | 13C | 12B | — | 8 | 12 |
| 5 | 3A | 11C | — | 11 | 11 | 16 |
| 9 | 2 | 3B | 2A | — | 7 | 23 |
| 11 | 2 | 6B | 2A | — | 7 | 18 |
| 15 | 7E | 4A | 7E | — | 12 | 22 |
| 16 | 3A | 2 | — | 2A | 4 | 7 |
| 17 | 2 | 1B | 2A | — | 7 | 20 |
| 19 | 3B | 11E | — | 11E | 15 | 17 |
| 20 | 7A | 7A | 7A | — | 28 | 28 |
| 21 | 14 | 7A | 8A | — | 10 | 28 |
| 24 | 3B | 11E | — | 11E | 9 | 17 |
| 26 | 11B | 3A | 11 | — | 10 | 11 |
| 29 | 3B | 3B | 3C | — | 9 | 11 |
| 41 | 13C | 8 | — | 8A | 12 | 21 |
| 44 | 2 | 3B | 2A | — | 7 | 9 |
| 46 | 14 | 3B | 8A | — | 10 | 15 |
| 48 | 3B | 7A | — | 7A | 14 | 28 |

Haplotypes defined by BoLA-DRB3 PCR-RFLP and BoLA-DRB and BoLA-DQB RFLPs

All haplotype information was derived from typing of workshop animals. For most animals, haplotypes were inferred from population data (Bernoco et al., 1992). By conventional RFLP typing, 31 DRB/DQB haplotypes were inferred among the 48 workshop animals. By comparison, 31 DRB3/DQB haplotypes could be identified in the same animals by combining workshop DQB RFLP data with our PCR-RFLP typing of DRB3 exon 2. Within these 31 haplotypes, 12 of the DRB3 alleles identified by PCR-RFLP matched patterns predicted for sequenced alleles. Eight DRB3/DQB haplotypes contained seven new DRB3 alleles (DRB3.2*10, *12, *16, *17, *18, *23, and *25) that were correctly predicted by DRB/DQB haplotypes with defined DRB allelic patterns, but contain DRB3 genes with sequences that have not been reported. The corresponding DRB RFLP patterns for the remaining 11 DRB3/DQB haplotypes were not determined by the workshop, but the DQB allele was either new or previously defined. These represent 11 new DRB3/DQB haplotypes: DRB3.2*4/ DQB*3A, DRB3.2*9/DQB*3B, DRB3.2*11/DQB*3A, DRB3.2*11/DQB*3B, DRB3.2*12/DQB*13C, DRB3.2*14/DQB*3B, DRB3.2*15/DQB*3B, DRB3.2*18/ DQB*6B, DRB3.2*20/DQB*1B, DRB3.2*22/DQB*4A, and DRB3.2*23/DQB*3B. The undefined DRB RFLP patterns in workshop animals 20 and 21 probably correspond to DRB*7A and not a new DRB RFLP pattern because both these haplotypes contained DRB3.2*28 and DQB*7A, which previously have been associated exclusively with DRB*7A.

The above data and discussion demonstrates that PCR-RFLP is a rapid method for identification of polymorphism in an expressed BoLA-DRB gene. The PCR-RFLP technique for BoLA-DRB3 typing is based upon the extensive polymorphism that is present in exon 2 of the BoLA-DRB3 gene, part of which can be detected with restriction endonucleases. PCR-RFLP typing of a genetically diverse sample of animals that was extensively studied in the Fourth International BoLA Workshop (Bernoco et al., 1992) resulted in the identification of DRB3 alleles that correspond to 12 of 14 known DRB3 sequences. In addition, 10 new DRB3 alleles were defined which had restriction patterns that were consistent with different combinations of restriction enzyme sites present among the sequenced alleles. One new allele (DRB3.2*16) contained a HaeIII site (position 173) that was not present in any of the published sequences. The position of this HaeIII site, as well as other restriction sites in DRB3.2*16 and DRB3.2*23, have been confirmed by DNA sequencing. PCR-RFLP typing of an additional sample of 120 animals of six cattle breeds lead to the definition of seven more alleles, of which three contained a 3 base pair deletion that mapped to the same restriction fragment as the 3 base pair deletion at codon 65 that was observed in DRB3.2*7 by Sigurdardóttir et al., (1991). It is thus possible that the 3 base pair deletions in DRB3.2*29, *30 and *31 also correspond to codon 65, which, if true, suggests that these alleles have diverged from a common ancestral allele.

Five restriction sites for RsaI, two for BstYI, and four for HaeIII were found among the 32 DRB3 alleles. See Table 1. All the restriction sites for these three enzymes are independent, because their recognition sequences do not overlap. Theoretically, $2^5=32$ different RsaI restriction fragment patterns are possible, of which 15 were identified in the current study. Similarly, $2^2=4$ BstYI, and $2^4=16$ HaeIII restriction patterns are theoretically possible, of which four BstYI and five HaeIII patterns were identified. Thus, based on currently known RsaI, BstYI and HaeIII sites, PCR-RFLP has the potential to distinguish between $2^5 \times 2^2 \times 2^4 = 2^{11} = 2048$ combinations of sites. Twice that number of DRB3 alleles is possible if the 3 base pair deletion is included as a source of variation.

The combination of conventional BoLA-DRB and BoLA-DQB RFLP analysis and PCR-RFLP typing of the BoLA-DRB3 gene resolved the presence of 38 DRB/DQB haplotypes among the animals that were included in this study. However, it can be estimated that at least 46 DRB/DQB haplotypes must be present in cattle based on additional DRB RFLP types (Sigurdardóttir et al., 1988, Joosten et al., 1990, Bernoco et al., 1992). Most DRB3 alleles were found to be part of one or two class II haplotypes. Only DRB3.2*11 was present in three haplotypes; this allele was in linkage with either DQB*3A, DQB*3B or DQB*9B. DQB*3B was the only DQB RFLP type that was found in linkage with five different DRB3 alleles. Since recombination between DQB genes and DRB3 apparently is a rare event, this is a remarkable observation which could indicate the presence of a recombination hotspot in the DQB*3B-containing haplotype. It is noteworthy that the only difference between DQB*3A and DQB*3B is in a TaqI RFLP (8.6 kilobase ("kb") and 9.3 kb, respectively), and both are in linkage with the same DQA RFLP type (Bernoco et al., 1992). The 0.7 kb sequence that is present in DQB*3B but not in DQB*3A is therefore of interest with respect to the location of a putative recombination hotspot, perhaps similar to that found for the murine H-2 complex (Steinmetz et al., 1986).

A potential problem of PCR-RFLP typing of heterozygous individuals is preferential allele amplification, presumably because of mismatches in the regions of primer annealing or secondary structure, which leads to different efficiencies of amplification between alleles. Among the alleles detected, only DRB3.2*7 was found to amplify at an efficiency that is noticeably lower than for any of the other alleles (FIG. 3, lanes 2, 6 and 10). The basis for this observation is presently not understood; however, such understanding is not necessary for the practice of this invention.

Another factor that may complicate PCR-RFLP typing in heterozygous individuals is the formation of heteroduplexes. Heteroduplexes are PCR by-products that result from pairing between allelic complementary DNA strands that out compete the hybridization of oligonucleotides with their template strands (Meyers et al., *PCR Technology: Principles and Application for DNA Amplification* 71–88 (1989)). Only heteroduplexes that form during the last annealing step will not be dissociated and may cause problems in PCR-RFLP typing. When heteroduplexes are digested with restriction enzymes, only the restriction sites that are present in the same position in both alleles will be cut, whereas the restriction sites that are not shared between the alleles will not be cut. This can result in the appearance of additional bands on the gel that belong to neither of the allelic patterns. The sizes of these extra bands, which are usually fainter than the authentic bands, can be predicted from the restriction maps for any combination of DRB3 alleles (such a band (284 base pairs) was present in lane 5 of FIG. 3). However, because heteroduplexes form primarily in the later cycles of the PCR, when the concentration of DNA is high, such heteroduplexes can be largely avoided by standardization of the DNA template concentration between samples, and an optimal number of cycles in the second round of the PCR. Therefore, heteroduplexes do not pose a significant problem to the interpretation of PCR-RFLP patterns in the practice of this invention.

Finally, problems may arise in the assignment of DRB3 genotypes to unrelated heterozygous individuals because of overlapping fragment patterns between alleles. Ten pairs of genotypes (e.g. DRB3.2*2/DRB3.2*14 and DRB3.2*3/ DFB3.2*13) cannot be resolved from 528 genotypes possible with the 32 PCR-RFLP alleles that have been found to date. In such cases, digestion with an additional restriction endonuclease or typing of a related individual may solve the problem.

Similar PCR-RFLP systems have been described for humans based on polymorphism in the second exon of HLA-DQA1, HLA-DPB1, HLA-DQB1, HLA-DQB2, HLA-DRB1, HLA-DRB3 and HLA-DRB4 genes (Dekker et al., (1990); Maeda et al., *Human Immunology* 111–121 (1990); Maeda et al. (1989); and Uryu et al., (1991)). It is of interest that four out of five RsaI sites are conserved between the HLA-DRB1 and BolA-DRB3 genes (Uryu et al., (1990)). Only RsaI 217, which is present in 14 out of 19

BoIA-DRB3 RsaI patterns, was absent in the 23 HLA-DRB1 alleles studied by Uryu et al. (1990), whereas RsaI 17 was unique for the HLA-DRB1 gene. These results suggest that PCR-RFLP could be an excellent method for studying the evolution of the DRB3 gene in Bovidae other than cattle, such as Addax and Scimitar Horned Oryx, and other mammals as well. Results in Bovidae other than cattle, not specifically shown herein, have shown identical restriction fragment patterns, albeit with different combinations; thus, defining new alleles.

PCR-RFLP is a powerful and sensitive technique for determination of polymorphism in a functionally relevant domain of the BoLA-DRB3 gene. Furthermore, one restriction site for each enzyme used, RsaI 217, BstYI 182, and HaeIII 154 (FIG. 1) probes for polymorphism within codons for amino acids that are part of the putative antigen recognition site of class II molecules (Brown et al., 1988). PCR-RFLP does not involve the use of radioisotopes, unlike other DNA based typing methods. Routinely, DRB3 typing of approximately 25 animals per day can be accomplished by PCR-RFLP. In addition, PCR-RFLP has been a useful tool for screening and selection of DRB3 and DQB clones for DNA sequencing. The number of DRB3 alleles that can be clearly distinguished with PCR-RFLP has not yet been achieved with any other typing technique. A further advantage of this technique is that now that it has been herein developed and disclosed, the constituent testing elements can be readily made available as a non-radioisotopic diagnostic kit.

II. Linkage between the Polymorphic BoLA-DRB3 and Prolactin Genes

Elucidation of the linkage relationship between polymorphic BoLA-DRB3 genes and the Prolactin gene was performed as follows:

Sire Selection

One bull was selected for the mapping study based on preliminary screening of genomic DNA samples for heterozygosity at both the BoLA-DRB3 and PRL loci (see below). This bull was a known BoLA-A, Bf and BoLA-DQB heterozygote (Teutsch et al., Animal Biotechnology 1:185–199 (1991)). It was also determined the RFLP-defined BoLA-DRB haplotype of this bull to be DRB2A/DRB7E, under other nomenclature systems. Herein, the two BoLA-DRB3 alleles of this bull were termed DRB3.2*7 and DRB3.2*12, respectively. See Section I. above.

Sperm Sorting

Sperm were prepared for flow sorting as described by Li et al., A Companion to Methods in Enzymology 2:49–59 (1991). Sperm heads were sorted into wells of flexible microtiter plates using a FACStar$^{PLUS}$ cell sorter (Becton Dickinson, San Jose, Calif.). Sperm were lysed and neutralized essentially as described by Li et al. (1991) except that lysis was performed by incubation with 5 µl 200 mM KOH, 50 mMDTT for 15 min at 65° C. Reactions were neutralized by the addition of 5 µl 900 mMTris-HCl (pH 8.3), 300 mM KCl, 200 mMHCl.

PCR Conditions for DRB3 and PRL

Figure 4A:
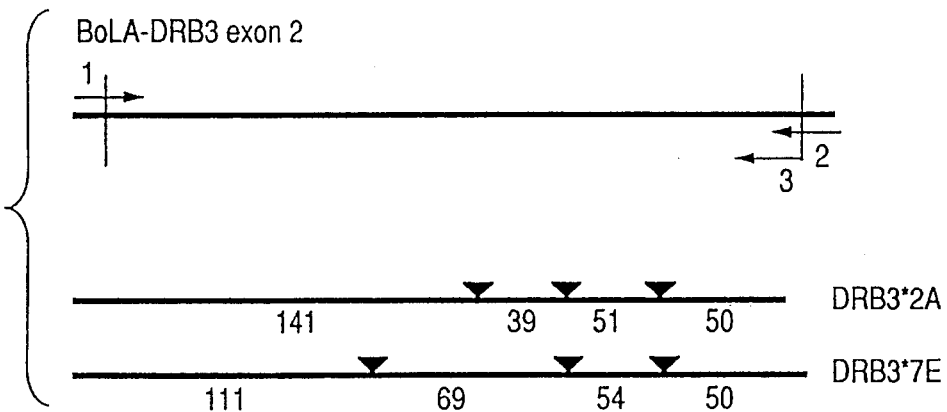
Figure 4B:
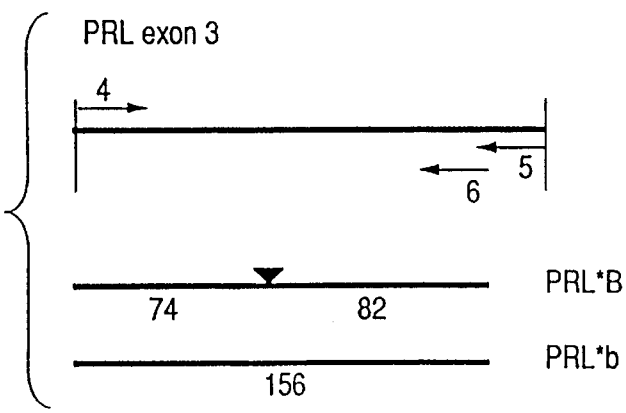

Oligonucleotide primers for the amplification of the second exon of BoLA-DRB3 are discussed above (primers HL030, HL031, and HL032, which respectively correspond to primers 1, 2, and 3 in FIG. 4a) and the primers for exon 3 of PRL were also selected according to previously published sequences (Sasavage et al., 1982); Sigurdardóttir et al., (1991)). The PRL primers are as follows: HL033: 5' CGAGTCCTTATGAGCTTGATTCTT 3' (SEQ ID NO:4), HL034: 5' CTGGCCAAATATCATCTCCATGCC 3' (SEQ ID NO:5), and HL035: 5' GCCTTCCA-GAAGTCGTTTGTTTTC 3' (SEQ ID NO:6), which respectively correspond to primers 4, 5, and 6 in FIG. 4b. The first round of PCR was carried out in 50 µl final volume containing K$^+$-free PCR buffer (final concentration 100 mM Tris-HCl, 2.5 mMMgCl$_2$, 0.01% gelatin), 100 µM dNTPs, 0.5 µM of each of the DRB3 primers (primers 1 and 2), 0.1 µM of each of the PRL primers (primers 4 and 5) and 1 unit of Taq polymerase (Perkin-Elmer Cetus, Norwalk, Conn.). Cycling conditions for the first round of PCR were: 92° C., 4 minutes followed by 10 cycles of 92° C., 1 minute, 60° C., 3 minutes and 72° C., 1 minute. This was followed by 30 cycles using the same conditions as above, except that the 60° C. annealing step was reduced to 2 minutes, followed by a final extension step of 72° C. for 5 minutes.

Heminesting (Li et al., (1990)) was used for the second round of PCR to increase the yield and specificity of PCR products (FIGS. 4a and b). There was some overlap between the 3' primers and the nested primers for both DRB3 (primers HL031 and HL032; eight bases, discussed above) and PRL (primers HL034 and HL035; three bases). Two microliters of the first round product were transferred to the wells of another microliter plate to which was added 48 µl of PCR buffer (as above but with KCl at a final concentration of 50 mM). The concentration of each primer was 0.5 µM in the final reaction; dNTPs and Taq polymerase were as described above. Second round amplifications for each locus were performed separately. Cycling conditions for the second round of PCR were 30 cycles of 92° C., 1 minute, 65° C., 30 seconds, followed by a final extension step of 72° C. for 5 minutes. All polymerase chain reactions with sperm were performed in a 96 well plate thermal cycler (MJ Research Inc., Cambridge, Mass.).

Genetic Analysis of PCR Products

The general strategies for discrimination of DRB3, discussed above, and PRL alleles by RsaI digestion are shown in FIGS. 4a and b. In preliminary experiments, the conditions for PCR amplification and genetic typing of BoLA-DRB3 and PRL were established using dilutions of genomic DNA down to 0.01 ng or approximately 3 copies of the gene. The authenticity of the 284 base pair DRB3 second round PCR product was confirmed by digesting 5 µl of PCR product with TaqI, which cuts at one site that is conserved at codon 40 in all known BoLA-DRB3 alleles (Sigurdardóttir et al., 1991). Similarly, the 156 base pair heminested PRL amplification product was first verified using genomic DNA. Exon 3 of bovine PRL has one polymorphic RsaI site at the codon for amino acid 103 in the polypeptide (Sasavage et al., (1982)). For single sperm typing, 6 µl of the DRB3 and 4 µl of the PRL second round PCR products were combined and digested with 5 units of RsaI for 1.5 hours at 37° C. Samples were run in 6% polyacrylamide minigels for 45 min, stained with ethidium bromide (1.0 µg/ml) and photographed under ultraviolet illumination.

Statistical Analysis

PCR analysis of single sperm is not error free and therefore the data were analyzed using a maximum likelihood method (Cui et al., 1989; Goradia et al., 1991), which takes these errors into account and estimates their values and standard errors in addition to the recombination fraction θ. A general model and various submodels (Cui et al., 1989) were tested on the data. The submodels tested differ from the general model in the assumptions made about amplification efficiency and contamination rate. The purpose of testing the submodels is to have the simplest model that best explains the data. Each submodel was compared to the general model using a likelihood ratio test and the "goodness of fit" of the data to the model was tested using a chi-square test.

Figure 5:
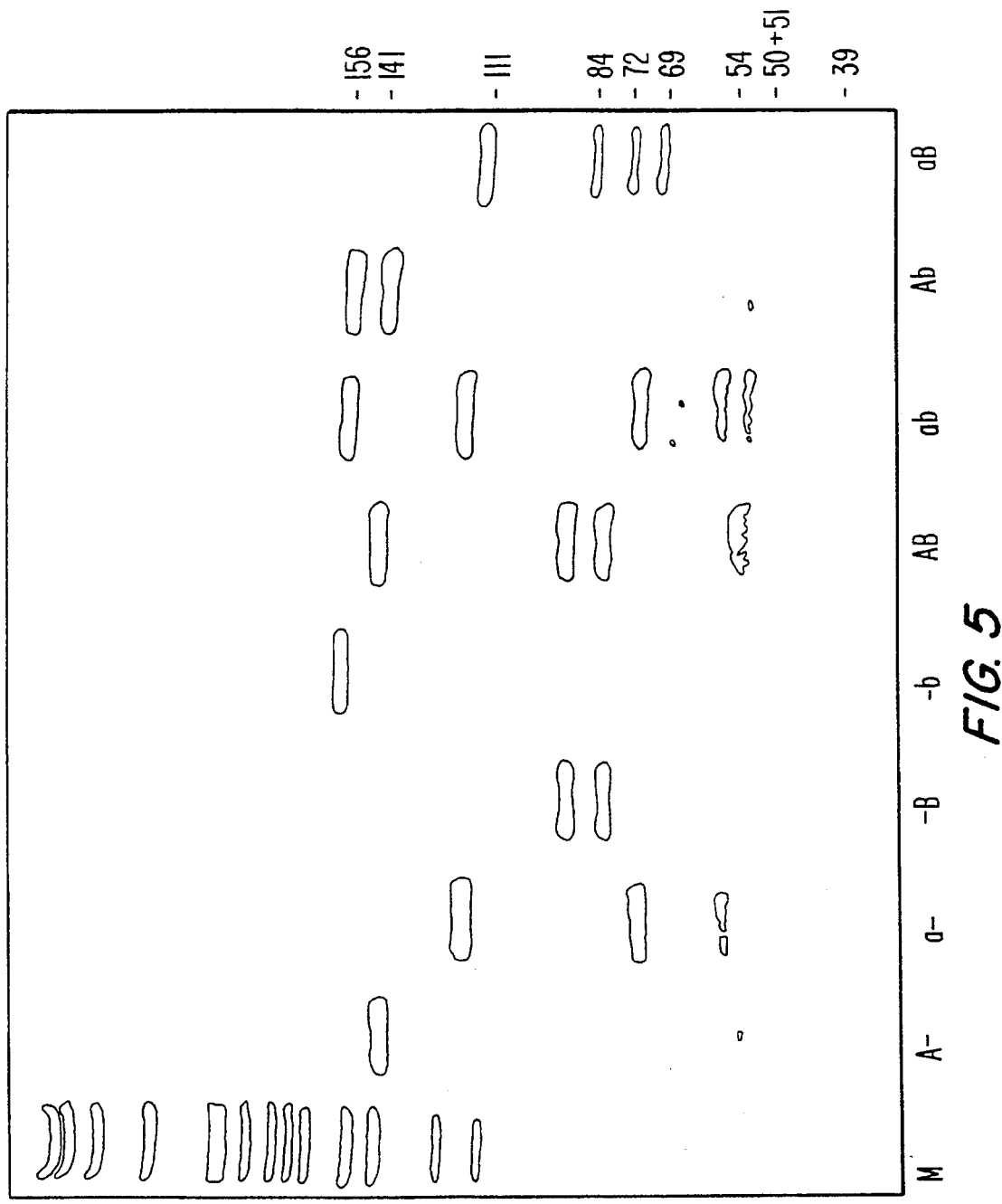

PCR-RFLP typing was performed on 300 sperm to analyze the segregation pattern of both PRL and DRB3 alleles. The RsaI fragments that define the two BoLA-DRB3 alleles were easily distinguished with single sperm (FIG. 5). The DRB3.2*7 (pattern e in Table 1) allele is defined by 141, 50, 51 and 39 base pair fragments, exactly matching the predicted restriction sites for this allele based on DNA sequencing (Sigurdardóttir et al., 1991). The DRB3.2*12 (pattern h in Table 1) allele is defined by 111, 69, 54 and 50 base pair RsaI restriction fragments. The two PRL alleles were distinguished-after RsaI digestion as 156 base pairs ("b" allele) or 82+74 base pairs ("B" allele) fragments. Alleles of both DRB3 and PRL could unambiguously be determined in ethidium bromide-stained 6% polyacrylamide minigels (FIG. 5).

The distribution of DRB3 and PRL alleles observed for 300 typed sperm is shown in Table 3 and the results of maximum likelihood analysis in Table 4. In Table 3, locus A is DRB3 and locus B is PRL. The DRB3.2*7 allele is defined by "A", and the DRB3.2*12 allele is defined by "a". The PRL allele which contains one RsaI site in exon 3 is defined by "B" (PRL*B), and the allele with no RsaI site is defined by "b" (PRL*b). See FIGS. 4a and b.

For maximum likelihood estimation of the recombination fraction θ (see Table 4), a general model and six submodels were tested. The general model (Cui et al., 1989) assumes no constraints on efficiency and contamination parameters (i.e., efficiency and contamination may be allele specific). Regardless of which model was tested, the value of θ and its standard error were virtually the same. Furthermore, the general model, which is considered the most applicable since it allows for variable rates of amplification efficiency and contamination, showed an excellent fit to the data (chi-square equaled 0.9478; 4 df). Therefore, the general model was accepted and evaluated.

The 95 percent confidence intervals for sperm typing parameters indicate at least 84% of the wells contained one sperm, a high efficiency of amplification of all alleles and low levels of contamination (Table 5). The estimate of the recombination fraction between DRB3 and PRL under the general model was θ=0.0403±0.0151. These values do not differ appreciably from the crude estimate of θ obtained simply by dividing the number of "recombinants" (Ab+aB) by the total number of informative sperm (AB+ab+Ab+aB)= 9/204=0.0441. The standard error of this estimate is [θ(1−θ)/n]$^{1/2}$=0.0143. Using this same rough method of estimation of allele frequencies, segregation of the DRB3 and PRL alleles did not deviate significantly from the expected 1:1 Mendelian ratio.

TABLE 3

| Observed sperm type | | | | No. observed |
|---|---|---|---|---|
| — | a | — | b | 108 |
| A | — | B | — | 87 |
| — | a | B | — | 5 |
| A | — | — | b | 4 |
| A | — | — | — | 6 |
| — | a | — | — | 15 |
| — | — | B | — | 28 |
| — | — | — | b | 14 |
| A | a | — | — | 0 |
| — | — | B | b | 0 |
| A | — | B | b | 1 |

TABLE 3-continued

| Observed sperm type | | | | No. observed |
|---|---|---|---|---|
| — | a | B | b | 2 |
| A | a | B | — | 3 |
| A | a | — | b | 2 |
| A | a | B | b | 3 |
| — | — | — | — | 22 |

TABLE 4

| Parameter | Estimate | SE | 95% C.I. |
|---|---|---|---|
| θ | 0.0403 | 0.0152 | 0.0106–0.0700 |
| Efficiency:A | 0.7525 | 0.0406 | 0.6728–0.8321 |
| Efficiency:a | 0.8910 | 0.0316 | 0.8291–0.9529 |
| Efficiency:B | 0.9400 | 0.0261 | 0.8888–0.9912 |
| Efficiency:b | 0.8846 | 0.0313 | 0.8233–0.9459 |
| Contamination:A | 0.0116 | 0.0122 | 0.0–0.0355 |
| Contamination:a | 0.0250 | 0.0182 | 0.0–0.0606 |
| Contamination:B | 0.0037 | 0.0139 | 0.0–0.0308 |
| Contamination:b | 0.0026 | 0.0093 | 0.0–0.0209 |
| 0 sperm | 0.0642 | 0.0167 | 0.0315–0.0970 |
| 1 sperm | 0.8937 | 0.0272 | 0.8404–0.9471 |
| 2 sperm | 0.0420 | 0.0238 | 0.0–0.0886 |

Usefulness of PCR-RFLP to Characterize Linked DRB3 and PRL

The sperm typing technique was used to obtain an estimate of the genetic distance between bovine PRL and BoLA-DRB3 in cattle. Linkage between these two genes was expected because: 1) these two genes comprise a conserved syntenic group in both man and cattle (Womack, 1991); and 2) in humans, physical mapping methods have placed PRL relatively close to HLA (6p23-6p21.1 and 6p21.3, respectively (Spence et al., (1989)). Assuming some conservation of linkage distances, PRL was expected to be less than 20 cM from DRB3 since PRL is placed within polymorphic flanking markers no more than 25 cM apart in the composite map of HSA6 (Keats et al., *Cytogenetic Cell Genetics* 51:459–502 (1989); Blanche et al., *Genomics* 9:420–428 (1991)). These results show, at least for this bull, that bovine PRL and DRB3 are tightly linked with θ=0.0403. These results demonstrate the general applicability of the sperm typing procedure to gene mapping problems in species other than humans and provide an example of how parallel mapping efforts in agriculturally important species of animals can have a positive impact on the development of the human linkage map. Furthermore, the power of DRB3 PCR-RFLP typing for linkage mapping on this chromosome is demonstrated.

Estimates for efficiencies of amplification and contamination rates used herein are generally consistent with previous human sperm typing studies (Cui et al., 1989; Li et al., 1990). Efficiency of amplification of the DRB3.2*7 allele was somewhat less than DRB3.2*12, which may be due to the extreme polymorphism of the BoLA-DRB3 gene, perhaps in the regions of primer annealing. In support of this argument, some preferential amplification of the DRB3.2*7 allele in heterozygous genomic DNA samples has been observed. The overall amplification efficiency of DRB3.2*7 (≈75%) did not seriously affect the outcome of the experiment and was taken into consideration by the maximum likelihood analysis employed.

The relationship between BoLA polymorphism and resistance to infectious diseases has been described and selection based on BoLA genotype has been suggested as a means of achieving resistance to specific diseases (Lewin et al., (1991)). The close linkage between BoLA-DRB3, which is highly polymorphic as described above, and PRL may be of practical significance as well. Recently, Cowan et al. (1990) found that the progeny of a bull that inherited one RFLP-defined PRL allele had greater genetic potential for milk production than offspring that inherited the alternative paternal allele, suggesting that PRL or a closely linked gene affects this economically important trait. If this observation is due to linkage, it is reasonable to predict that the closely linked BoLA system will be a better marker than PRL for this QTL (milk production) because BoLA is highly polymorphic, thus enabling the dissection of many more possible haplotypes. Thus, a diagnostic kit as discussed above can be created to test whether polymorphism in DRB3 can be a predictor of possibly linked traits such as milk production.

A variety of methods have been previously used to type alleles present in PCR products obtained from single sperm (reviewed in Li et al., 1991). These include allele specific hybridization probes, and allele discrimination by primer length which converts nucleotide difference(s) into a length polymorphism (Li et al., 1990). The mapping strategy employed RsaI for discrimination of DRB3 and PRL alleles. However, other restriction enzymes may be employed for further discrimination among alleles. For instance, as described above, HaeIII and BstYI provided further discrimination of BoLA-DRB3. See FIG. 1 and associated discussion. These results add restriction enzyme analysis to other allele detection systems used for sperm typing. The restriction enzyme analysis technique can be fast and inexpensive, does not require the use of radioisotopes and many of the steps have the potential for automation. Of course, with restriction enzyme analysis the detection of DNA sequence variation is limited to restriction enzyme recognition sequences.

A 10 to 20 cM resolution map of the bovine genome is generally regarded as a prerequisite to the identification of polymorphic genes affecting economically important traits, designated herein "economic trait loci" or "ETL", such as growth, reproduction and lactation. As a mapping method, sperm typing has the disadvantage that sequence information must be known. Furthermore, a genetic map based on this method will be male-specific and this may be inadequate for marker-assisted selection schemes which utilize females for genetic improvement, such as multiple ovulation embryo transfer. In addition, quantitative traits cannot be measured on sperm, so sperm typing cannot be used to map ETL. However, the use of polymorphic markers such as BoLA-DRB3 for insights into milk production should be appropriate.

The utilization of ETL for genetic improvement via marker-assisted selection (Fernando et al., *Genetic Selection and Evolution* 21:467–477 (1989)) will require very accurate genetic maps. The sperm typing technique has a distinct advantage for generating linkage maps over Southern blot-based RFLP analysis of pedigreed families because large numbers of meiotic products can be scored for segregation of alleles. Very low standard errors for θ can be obtained in this way. Furthermore, sperm typing is particularly useful for mapping genes which have skewed allele frequencies, as only a single doubly heterozygous male is needed for a two-locus mapping experiment. The wide availability of bull semen through commercial artificial insemination organizations and private breeders will accelerate the search for suitable donors for specific mapping experiments. With the increasing rate of new sequence information in cattle, the sperm typing technique can contribute significantly to the development of a low to moderate resolution genetic map of the bovine genome.

III. Use of PCR-RFLP for Other Diagnostic Assays—Motif Discrimination by Product Length Typing by PCR-RFLP is also useful for creating and/or standardizing other diagnostic assays. Because polymorphism in the BoLA-DRB3 gene in cattle correlates to resistance or susceptibility to various bovine diseases, such as persistent lymphocytosis ("PL"), sequence data of the BoLA-DRB3 is useful as a predictor of disease resistance and susceptibility. Based on the results of PCR-RFLP typing for PL in cattle caused by bovine leukemia virus ("BLV") infection, the complete nucleotide sequence of DRB3 alleles from resistant and susceptible animals were determined. Among resistant haplotypes the amino acids glutamic acid (E in single letter code, this code is used throughout this section) and arginine (R) were found exclusively at positions 70 and 71 respectively in the DRB3 β-chain peptide (SEQ ID NO:7). Based on the predicted structure of class II molecules, positions 70 and 71 are part of the antigen recognition site contained within the alpha helix and face into the peptide binding groove. Through the use of the PCR-RFLP data, a new predictive diagnostic assay was developed for cattle which is based upon identification and detection of amino acid motifs of interest, the components of which can be made available as a non-radioisotopic diagnostic kit, which employs a polymerase chain reaction. See above. With this assay, termed motif discrimination by product length ("MDPL"), no animals (cattle) with PL (now more than 50 tested) have ever been identified that have the amino acid motif of interest E and R at positions 70 and 71 (amino terminal to carboxyl terminal). Thus, cattle having the E and R motif in at least one allelic DRB3 product is absolutely correlated with resistance to PL. The use of MDPL requires only one amino acid motif, E and R, to predict resistance to PL; whereas with PCR-RFLP, resistance is associated with multiple types, each of which encode E and R ("ER") at positions 70 and 71 respectively. Thus, MDPL simplifies the identification of PL resistance genes.

Figure 6A:
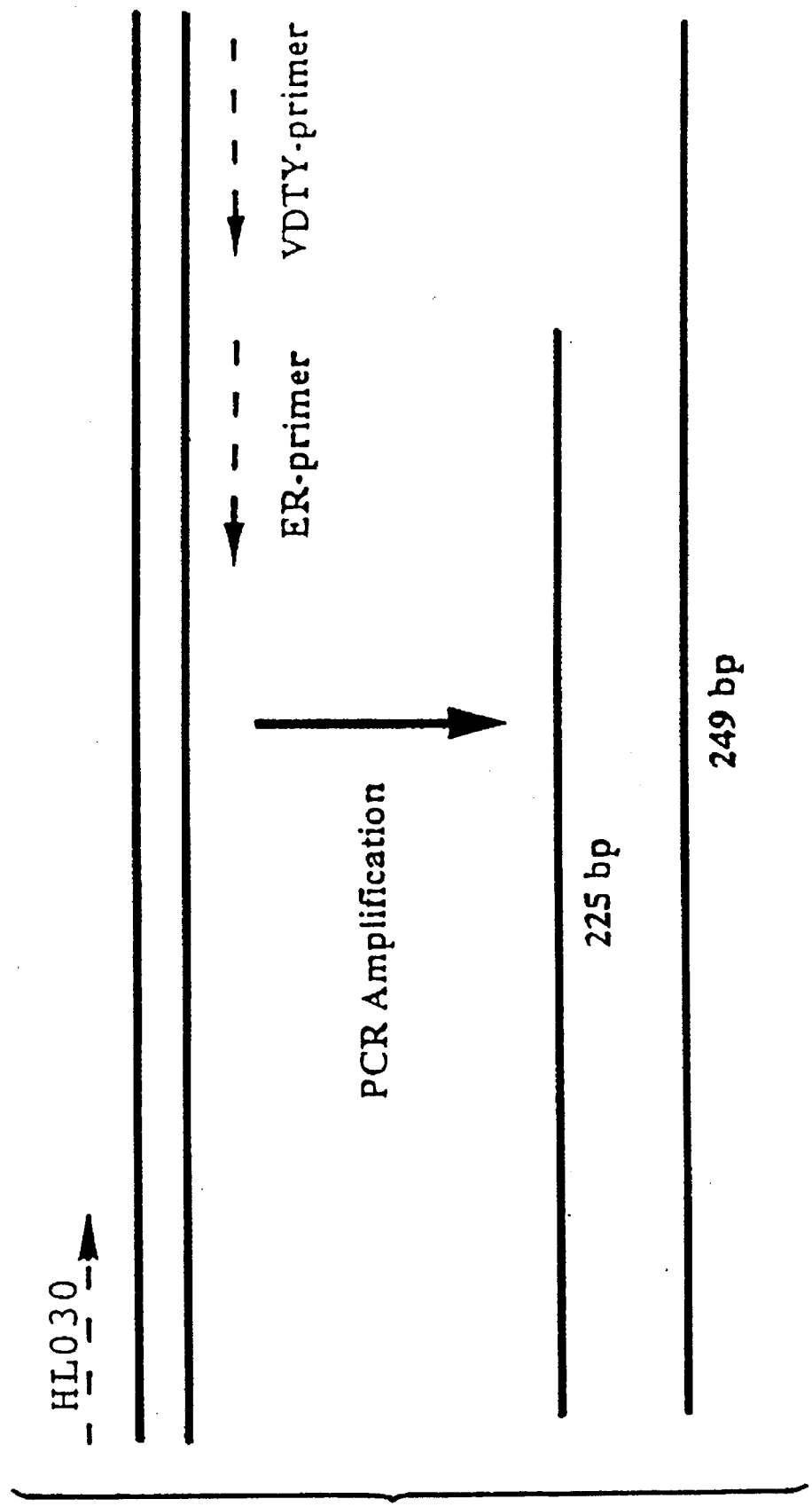

Testing for ER at positions 70 and 71 is accomplished using the ER primer. The general scheme of this PCR amplification and testing is shown in FIG. 6a. The PCR annealing reaction should occur under stringent conditions, i.e. 62° C. for 15 seconds. As shown in FIG. 6b, the ER primer has a sequence of 5' GCCCGCCTCTCCTCCAG 3', see SEQ ID NO:8, which anneals to the complementary strand (SEQ ID NO: 11), also shown in FIG. 6b, in alleles which encode ER at positions 70 and 71. The HL030 primer is also used. See SEQ ID NO:1. Alleles which encode ER at positions 70 and 71 are DRB3.2*11, DRB3.2*23, and DRB3.2*28. See FIG. 6b; Table 1. Presence of ER at positions 70 and 71 will be demonstrated by the production of a 225 base pair PCR product, which can be detected by ethidium bromide staining. See FIG. 6b. Alleles which encode motifs other than ER at positions 70 and 71, such as glutamic acid-lysine (EK), arginine-glycine (RG), arginine-glutamic acid (RE) or glycine-arginine (GR), do not permit PCR extension with the ER primer under stringent reaction conditions due to mismatches indicated in the left hand column of FIG. 6b. These alleles, respectively DRB3.2*24, DRB3.2*8, DRB3.2*16, and DRB3.2*22, will produce negative results with MDPL because a 225 base pair PCR product will not be formed.

Susceptibility in cattle to PL also has a genetic basis that maps to BoLA-DRB3. Among the DRB3 alleles from susceptibility-associated BoLA haplotypes, the amino acid motif of interest valine-aspartic acid-threonine-tyrosine (V, D, T and Y in the single letter code, hereinafter "VDTY", (SEQ ID NO:9)) at positions 75–78 (amino terminal to carboxyl terminal) was most commonly found in animals with PL. This motif is part of the DRB3 molecule that is recognized by T cells. Typing by MDPL can therefore also be used to directly test for susceptibility of cattle to PL by detecting VDTY and related motifs in the DRB3 gene.

Testing for VDTY at positions 75 through 78 is accomplished using the VDTY primer. The general scheme of this amplification and testing is also shown in FIG. 6a. As shown in FIG. 6b, the VDTY primer has a sequence of 5' GTCT-GCAGTACGTGTCCAC 3', see SEQ ID NO:10, which anneals to the complementary strand (SEQ ID NO.12), also shown in FIG. 6b, in alleles which encode VDTY at positions 75 through 78. As was the case for ER, the HL030 primer is also used. See SEQ ID NO:1. Alleles which encode VDTY at positions 75 through 78 include DRB3.2*8 and DRB3.2*16. See FIG. 6b; Table 1. Other alleles also encode VDTY. See Sigurdardóttir et al., *Animal Genetics* 22:199–209 (1991). Presence of VDTY at positions 75 through 78 will be demonstrated by the production of a 249 base pair PCR product, which can be detected by ethidium bromide staining. See FIG. 6b. Alleles which encode motifs other than VDTY at positions 75 through 78, such as valine-aspartic acid-arginine-valine (VDRV) and valine-aspartic acid-threonine-valine (VDTV), do not permit PCR extension with the VDTY primer under stringent reaction conditions due to mismatches indicated in the left hand column of FIG. 6b. These alleles, which include DRB3.2*11, DRB3.2*23, DRB3.2*24, and DRB3.2*28 for VDRV, and DRB3.2*22 and DRB3.2*26 for VDTV identified to date, will produce negative results with MDPL because a 249 base pair PCR product will not be formed. Other alleles which encode VDRV or VDTV may also exist.

FIGS. 7a and 7b show the results achieved with MDPL with 13 cows with PL (FIG. 7a) and 13 seropositive non-PL cows (FIG. 7b) which were unrelated and age-matched to the PL cows. The lower band (225 base pairs, see FIG. 7b) is present when ER at positions 70 and 71 is encoded by one or both alleles. Under the annealing conditions used for this MDPL run, the larger fragment (249 base pairs) was produced if either VDTY or VDTV was present by one or both DRB3 alleles; however, VDRV (lanes 1 and 3) was distinguished. Higher annealing temperatures (i.e. 65° C.), which are more stringent, will distinguish between VDTY and VDTV. FIG. 7a demonstrates that not one of the cows with PL possesses the ER motif at positions 70 and 71, and VDTY or related motifs predominate in these cows.

The foregoing has concentrated on the preferred embodiments of the claimed invention. However, it is to be understood that changes in construction, combination, selection, and arrangement of the elements or steps of this invention may be resorted to without departing from the scope and spirit of the invention as claimed.

What is claimed is:

1. A method for evaluating resistance of an animal of the genus Bos to persistent lymphocytosis, comprising the steps of:
    obtaining a sample of DNA from said animal, wherein said DNA includes a DRB3 gene exon 2;
    identifying nucleotides of said DRB3 gene exon 2; and
    determining whether said nucleotides contain codons that encode a glutamic acid at position 70 and an arginine at position 71 of the DRB3 gene product, the presence of which codons indicates resistance to persistent lymphocytosis.

2. A method according to claim 1, wherein said identifying step employs a polymerase chain reaction and a primer.

3. A method according to claim 2, wherein said polymerase chain reaction is undertaken under stringency conditions where amplification can only occur if said codons that encode a glutamic acid and an arginine at positions 70 and 71, respectively of said DRB3 gene product are present.

4. A method according to claim 2, wherein said primer comprises a sequence according to SEQ ID NO:8.

5. A method for evaluating susceptibility of an animal of the genus Bos to persistent lymphocytosis, comprising the steps of:
    obtaining a sample of DNA from said animal, wherein said DNA includes a DRB3 gene exon 2;
    identifying nucleotides of said DRB3 gene exon 2; and
    determining whether said nucleotides contain codons that encode a valine at position 75, an aspartic acid at position 76, a threonine at position 77, and a tyrosine at position 78, of the DRB3 gene product, the presence of which codons indicates susceptibility to persistent lymphocytosis.

6. A method according to claim 5, wherein said identifying step employs a polymerase chain reaction and a primer.

7. A method according to claim 6, wherein said polymerase chain reaction is undertaken under stringency conditions where amplification can only occur if said codons that encode a valine at position 75, an aspartic acid at position 76, a threonine at position 77, and a tyrosine at position 78, of said DRB3 gene product are present.

8. A method according to claim 6, wherein said primer comprises a sequence according to SEQ ID NO:10.

9. A diagnostic kit for evaluating resistance of an animal of the genus Bos to persistent lymphocytosis comprising a primer that specifically hybridizes to that portion of a DRB3 gene exon 2 that contains codons that encode amino acid residues at positions 70 and 71 of the DRB3 gene product only when said DRB3 gene exon 2 portion encodes a glutamic acid at said position 70 and an arginine at said position 71 and wherein hybridization of the primer to said portion of the DBR3 exon 2 indicates resistance to persistent lymphocytosis.

10. A diagnostic kit according to claim 9, wherein said primer comprises a sequence according to SEQ ID NO:8.

11. A diagnostic kit for evaluating susceptibility of an animal of the genus Bos to persistent lymphocytosis comprising a primer that specifically hybridizes to that portion of a DRB3 gene exon 2 that contains codons that encode amino acid residues at positions 75 through 78 of the DRB3 gene product only when said DRB3 gene exon 2 portion encodes a valine at said position 75, an aspartic acid at said position 76, a threonine at said position 77, and a tyrosine at said position 78 and wherein hybridization of the primer to said portion of the DBR3 exon 2 indicates susceptibility to persistent lymphocytosis.

12. A diagnostic kit according to claim 11, wherein said primer comprises a sequence according to SEQ ID NO 10.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( v i i ) IMMEDIATE SOURCE:
        ( B ) CLONE: HL030

( x i ) SEQUENCE DESCRIPTION: SEQ ID NO:1:

ATCCTCTCTC TGCAGCACAT TTCC        24

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: YES ( v i i ) IMMEDIATE SOURCE:
        ( B ) CLONE: HL031

( x i ) SEQUENCE DESCRIPTION: SEQ ID NO:2:

TTTAAATTCG CGCTCACCTC GCCGCT                                                                      26

( 2 ) INFORMATION FOR SEQ ID NO:3:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i i ) HYPOTHETICAL: NO ( i v ) ANTI-SENSE: YES ( v i i ) IMMEDIATE SOURCE:
       ( B ) CLONE: HL032

( x i ) SEQUENCE DESCRIPTION: SEQ ID NO:3:

TCGCCGCTGC ACAGTGAAAC TCTC                                                                        24

( 2 ) INFORMATION FOR SEQ ID NO:4:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i i ) HYPOTHETICAL: NO ( i v ) ANTI-SENSE: NO ( v i i ) IMMEDIATE SOURCE:
       ( B ) CLONE: HL033

( x i ) SEQUENCE DESCRIPTION: SEQ ID NO:4:

CGAGTCCTTA TGAGCTTGAT TCTT                                                                        24

( 2 ) INFORMATION FOR SEQ ID NO:5:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i i ) HYPOTHETICAL: NO ( i v ) ANTI-SENSE: YES ( v i i ) IMMEDIATE SOURCE:
       ( B ) CLONE: HL034

( x i ) SEQUENCE DESCRIPTION: SEQ ID NO:5:

CTGGCCAAAT ATCATCTCCA TGCC                                                                        24

( 2 ) INFORMATION FOR SEQ ID NO:6:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i i ) HYPOTHETICAL: NO ( i v ) ANTI-SENSE: YES ( v i i ) IMMEDIATE SOURCE:
       ( B ) CLONE: HL035

( x i ) SEQUENCE DESCRIPTION: SEQ ID NO:6:

GCCTTCCAGA AGTCGTTTGT TTTC     24

( 2 ) INFORMATION FOR SEQ ID NO:7:

( i ) SEQUENCE CHARACTERISTICS:
      ( A ) LENGTH: 2 amino acids
      ( B ) TYPE: amino acid
      ( D ) TOPOLOGY: linear ( x i ) SEQUENCE DESCRIPTION: SEQ ID NO:7:

Glu Arg
   1

( 2 ) INFORMATION FOR SEQ ID NO:8:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: YES ( v i i ) IMMEDIATE SOURCE:
      ( B ) CLONE: ER primer ( x i ) SEQUENCE DESCRIPTION: SEQ ID NO:8:

GCCCGCCTCT CCTCCAG     17

( 2 ) INFORMATION FOR SEQ ID NO:9:

( i ) SEQUENCE CHARACTERISTICS:
      ( A ) LENGTH: 4 amino acids
      ( B ) TYPE: amino acid
      ( D ) TOPOLOGY: linear ( x i ) SEQUENCE DESCRIPTION: SEQ ID NO:9:

Val Asp Thr Tyr
   1

( 2 ) INFORMATION FOR SEQ ID NO:10:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: YES ( v i i ) IMMEDIATE SOURCE:
      ( B ) CLONE: VDTY primer ( x i ) SEQUENCE DESCRIPTION: SEQ ID NO:10:

GTCTGCAGTA CGTGTCCAC     19

( 2 ) INFORMATION FOR SEQ ID NO:11:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: NO ( x i ) SEQUENCE DESCRIPTION: SEQ ID NO:11:

CTGGAGGAGA GGCGGGC 17

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:12:

GTGGACACGT ACTGCAGAC 19